(12) United States Patent
Steber et al.

(10) Patent No.: US 6,593,754 B1
(45) Date of Patent: Jul. 15, 2003

(54) COMPACT SUBSURFACE OBJECT LOCATOR

(75) Inventors: George R. Steber, Mequon, WI (US); Thomas M. Luebke, Menomonee Falls, WI (US); Stephen J. Skeels, Milwaukee, WI (US); David L. Wiesemann, Pewaukee, WI (US)

(73) Assignee: Actuant Corporation, Glendale, WI (US)

( * ) Notice: Subject to any disclaimer, the term of this patent is extended or adjusted under 35 U.S.C. 154(b) by 0 days.

(21) Appl. No.: 09/538,087

(22) Filed: Mar. 29, 2000

Related U.S. Application Data

(60) Provisional application No. 60/127,322, filed on Apr. 1, 1999.

(51) Int. Cl.[7] .................... G01R 27/26; G01R 19/00; G01N 27/72
(52) U.S. Cl. .................... 324/671; 324/67; 324/228
(58) Field of Search .................... 324/457, 67, 671, 324/228, 642, 329, 156, 133, 658, 663, 686, 690; D14/426, 399, 453

(56) References Cited

U.S. PATENT DOCUMENTS

| 3,742,341 A | * | 6/1973 | Clowes et al. ............ 324/329 |
| 4,099,118 A | | 7/1978 | Franklin et al. ............ 324/671 |
| 4,270,041 A | * | 5/1981 | Pleyber ............ 377/19 |
| 4,310,797 A | * | 1/1982 | Butler ............ 324/228 |
| 4,464,622 A | | 8/1984 | Franklin ............ 324/67 |
| 4,481,814 A | * | 11/1984 | Wentzell ............ 73/866.5 |
| 4,613,816 A | * | 9/1986 | Zeamer ............ 324/248 |
| 4,853,617 A | * | 8/1989 | Douglas et al. ............ 324/67 |
| 4,992,741 A | * | 2/1991 | Douglas et al. ............ 324/671 |
| 5,024,236 A | * | 6/1991 | Shapiro ............ 600/548 |
| 5,304,207 A | * | 4/1994 | Stromer ............ 607/3 |
| 5,352,974 A | * | 10/1994 | Heger ............ 324/67 |
| 5,457,394 A | * | 10/1995 | McEwan ............ 324/642 |
| 5,485,092 A | | 1/1996 | Fortin ............ 324/457 |
| 5,512,834 A | * | 4/1996 | McEwan ............ 324/642 |
| 5,619,128 A | * | 4/1997 | Heger ............ 324/67 |
| 5,812,057 A | * | 9/1998 | Hepworth et al. ............ 340/540 |
| 5,917,314 A | * | 6/1999 | Heger et al. ............ 324/67 |
| D419,546 S | | 1/2000 | Krantz et al. ............ D14/426 |
| 6,023,159 A | * | 2/2000 | Heger ............ 324/67 |
| 6,129,668 A | * | 10/2000 | Haynor et al. ............ 600/424 |
| 6,215,293 B1 | * | 4/2001 | Yim ............ 324/67 |
| 6,229,294 B1 | * | 5/2001 | Wun ............ 324/67 |

FOREIGN PATENT DOCUMENTS

| GB | 2238201 A | * | 11/1989 | |
| WO | WO-00/79305 A1 | * | 12/2000 | ............ G01V/3/15 |

* cited by examiner

Primary Examiner—N. Le
Assistant Examiner—Wasseem H. Hamdan
(74) Attorney, Agent, or Firm—Quarles & Brady LLP

(57) ABSTRACT

A hand held subsurface object locator has a pocket sized housing that contains circuitry and a power source for electrically detecting substratum objects hidden behind a surface. The housing is preferably less than two inches wide and at least three times as long as it is wide. The housing has a pocket clip preferably affixed to a battery compartment door at one end of the housing and the other end of the housing is tapered and includes a plurality of tapered indicators.

5 Claims, 9 Drawing Sheets

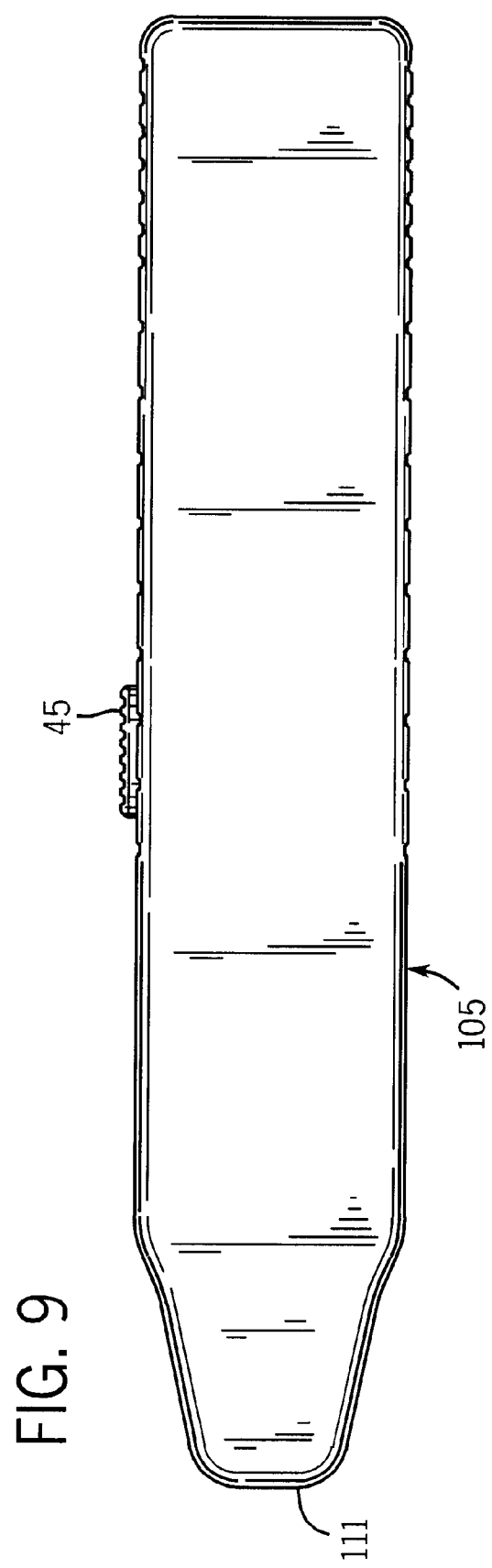

COMPACT SUBSURFACE OBJECT LOCATOR

CROSS REFERENCE TO RELATED APPLICATIONS

This claims the benefit of U.S. Provisional Patent Application No. 60/127,322 filed Apr. 1, 1999.

STATEMENT CONCERNING GOVERNMENT SPONSORED RESEARCH OR DEVELOPMENT

Not Applicable.

FIELD OF THE INVENTION

This invention relates to electronic instruments for detecting a stud or other object behind an opaque surface, such as wall board.

BACKGROUND OF THE INVENTION

Carpenters, electricians, do-it-yourselfers and others are often faced with the problem of locating the position of the wall studs behind the wall board material forming the wall surface. They are interested in hanging pictures, drilling holes and so on. However after the walls arc finished and painted the location of the hidden substructure (i.e. the studs) is not visually detectable. The same is true of finding the location of hidden wooden frames in furniture and boats from the outside surface of the structure.

U.S. Pat. No. 4,099,118 issued Jul. 4, 1978 discloses an electronic wall stud sensor which is suitable for detecting a wall stud behind a wall surface. It utilizes one or more capacitor plates, a fixed frequency oscillator, a dual one-shot multivibrator, a field effect transistor, and a complicated calibration procedure. Each individual circuit must be calibrated at the time of manufacture, which is a costly procedure for mass production.

U.S. Pat. No. 4,464,622 describes a wall stud sensor similar to U.S. Pat. No. 4,099,118 but with a plurality of capacitor elements and means for detecting the presence of alternating current in the wall. Finding the presence of alternating current in walls is often not practical or possible with modem wiring methods. U.S. Pat. No. 5,352,974 describes a stud sensor similar to U.S. Pat. No. 4,099,118 but with means for storing calibration data for thick or thin walls. However, in most cases, the user will not know if the wall is thick or thin. The circuit used is complex and uses special purpose hardware. The sensor also uses a plurality of capacitor plates. Both of these devices require factory calibration.

U.S. Pat. No. 5,485,092 describes a device for investigating surface and subsurface structures. It uses four-sided conductive elongated plates and rectangular sensor plates connected together in a special arrangement. The different surfaces are charged at different rates and a differential amplifier and peak detector are used to determine information about the subsurface. It requires a complicated charging scheme and an expensive voltmeter for readout, which requires an interpretation of the results which would be difficult for an inexperienced person.

Prior art sensors were required to be a relatively large size so as to make them sufficiently sensitive for their intended purpose. Prior circuits required a relatively large sensor, and to isolate the sensor from the user's hand, which contributed to the relatively large size of the sensors.

Thus, there is a need for a low cost subsurface object locator that is easy to use, works well in the environment for which it is designed, simply and reliably identifies the location of substructure components in an efficient manner, is easy to manufacture, requires no calibration or adjustments by the factory or operator, and can be made of a relatively small size.

SUMMARY OF THE INVENTION

The invention provides a compact device capable of efficiently finding the location of hidden objects or substrata such as studs, joists and other similar objects below the surface of walls, floors and similar type structures. The device may also be used to find the location of braces, wood frames or other substructures in wooden furniture such as tables and cabinets, wooden boats and similar type structures.

In particular, the invention provides a hand held subsurface object locator having a housing which contains a power source and circuitry operative to detect substratum objects hidden behind a surface which is probed with the locator by sliding the locator along the surface.

In one form, the locator housing is less than two inches wide. In another form, the locator housing is at least three times as long as it is wide. And in yet another form, the locator housing has a pocket clip.

One object of the invention is to provide a compact subsurface object locator that has a significantly smaller form factor than prior locators. For example, the circuitry of the locator of the present invention can be contained in a pen-light sized housing.

Another object of the invention is to provide a subsurface object locator that can be easily retained to a person's body. The locator of the present invention can fit easily into small hands as well as breast shirt pockets and pants pockets due to the small, narrow size of the housing.

Another object of the invention is to provide a compact subsurface object locator that is sufficiently sensitive to detect subsurface objects at the same or a larger depth range than prior devices. Compact circuitry including a small guard plate provide improved sensitivity, range, and depth of detection of the locator.

Yet another object is that the locator be easy to use, low cost to manufacture, require no factory calibration, and operate without critical manual adjustments on the part of the operator or the factory.

Other features and advantages of the invention will be apparent from the detailed description and drawings.

BRIEF DESCRIPTION OF THE DRAWINGS

FIG. 9 is a bottom plan view of the instrument,

DETAILED DESCRIPTION OF THE PREFERRED EMBODIMENT

Figure 1:
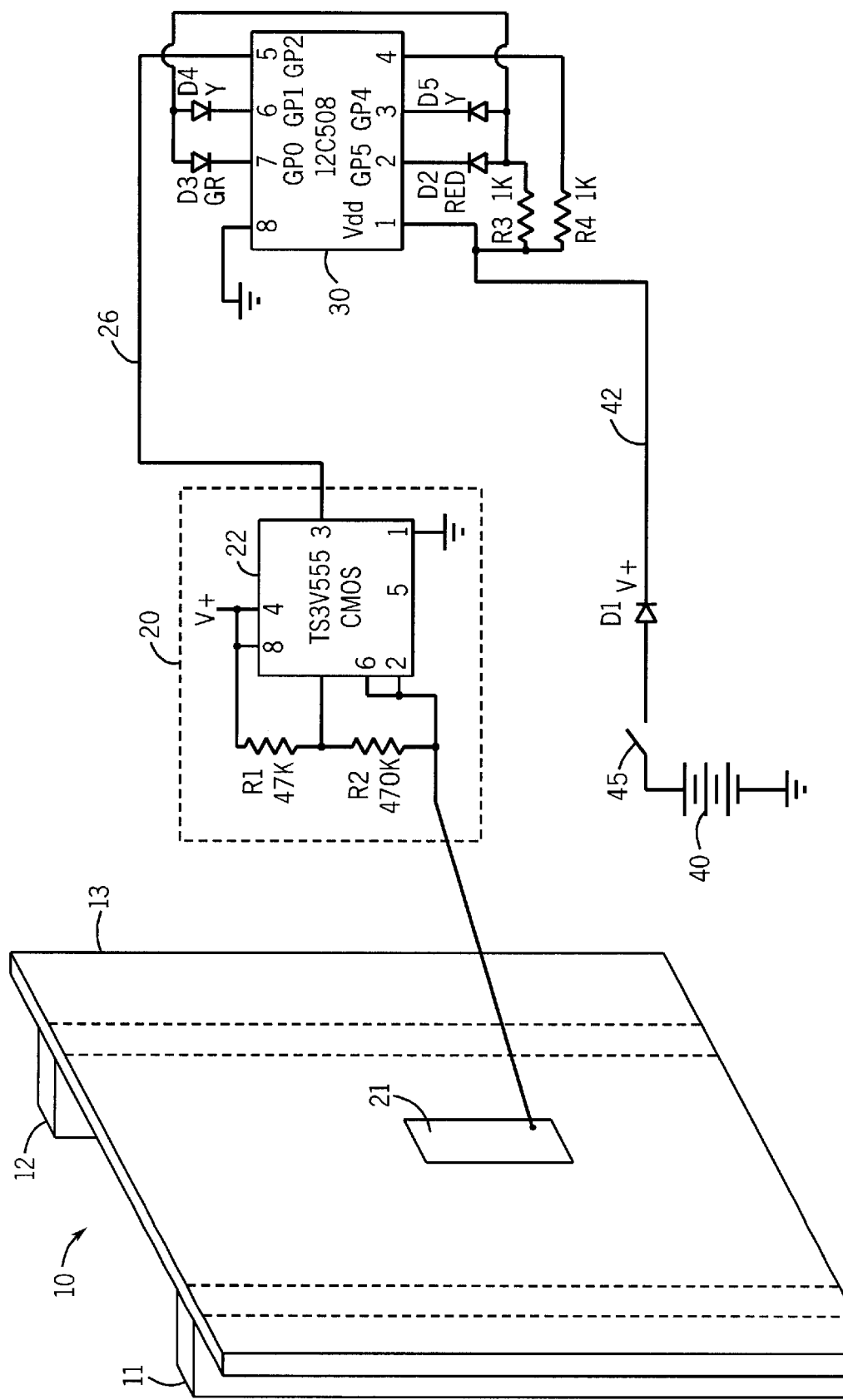
FIG. 1 is a schematic diagram of a first embodiment of a circuit for practicing the invention.

Referring first to FIG. 1 there is illustrated a circuit diagram of the invention. Shown on this figure is a portion of a wall structure 10, studs 11, 12 and wall board 13 to be illustrative of one way of operating the invention. In this case it is desired to locate the positions of the hidden studs 11 and 12. As shown in FIG. 1 there is a metallic sensor plate 21 connected to a CMOS oscillator 20 which produces a square (or rectangular) wave output. The circuit consists of a timer IC 22, the sensor plate and resistors. The frequency of the square (or rectangular) wave produced by the oscillator 20 is determined by the values of resistors R1 and R2 and the capacitance presented by the plate 21. When the sensor plate is above a section of the wall 13 with no studs it will cause the oscillator 20 to run at frequency f1. When the sensor is above a section of the wall 13 that has a stud below it the oscillator will have a different frequency f2.

The square (or rectangular) wave output of the oscillator 20 goes to a microprocessor circuit 30 via line 26. The microprocessor circuit 30 is programmed to measure the frequency difference f1 minus f2. The frequency difference has been found to be a reliable and consistent means of identifying subsurface objects such as studs and has been found to be relatively independent of the wall material. This makes the device self calibrating, obviating the need for any special factory calibration. If the frequency difference exceeds an amount deemed sufficient to indicate the presence of a stud, an LED is turned on.

The circuit 30 actually has four LEDs D2, D3, D4, D5 that can be activated at different amounts of frequency change. This is illustrated in more detail in FIG. 2, discussed later on. More or fewer LEDs could be used as indicators depending upon resolution and cost considerations. The circuit is powered by batteries 40 (four 1.5 V pancake cells) through protective diode D1 (e.g., a IN270 diode) and line 42. Resistor R3 is used to limit the current in the LEDs. Resistor R4 is used for a power on reset for circuit 30. Normally open switch 45 is pressed to enable power to circuit from the batteries 40 to circuit 30.

Although visual LED indicators D2–D5 are described here, it should be clear that audible indicators could be used as well. For example, different audible tones could be produced corresponding to various frequency differences encountered in scanning the wall, as the leading edge of a stud was approached, the frequency could go up, and as the trailing edge of the stud was passed the frequency could go down. In fact, there are occasions where audible indications may be better, such as in cases where the visible indicators may be hard to see.

Figure 2:
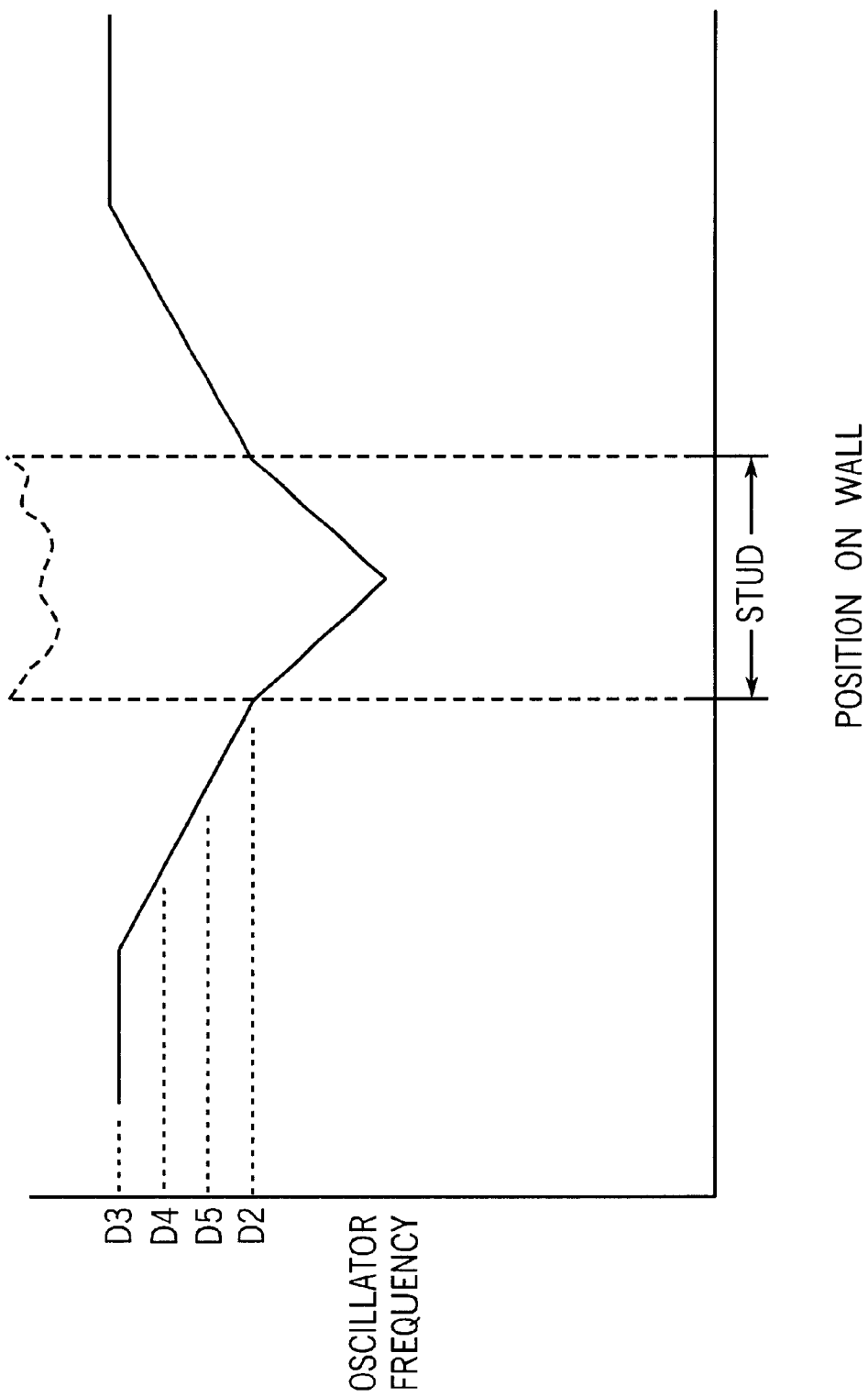
FIG. 2 shows various waveforms and details of operation of the circuit of FIG. 1.

Referring now to FIG. 2 there is illustrated the relation of the signal indicator means (LEDs) D2–D5 to the position of the sensor plate along the wall. As the sensor moves along the wall the frequency changes in accordance with curve 52. As the frequency decreases, the circuit 30 (FIG. 1) senses this change and turns on one or more of the LEDs D2–D5. The LEDs could be turned on so as to overlap in on-times or not. In the preferred embodiment, the on-times do not overlap to preserve battery power.

To use the device described, the plate 21 is placed on or in close proximity to wall 13 where there are no studs and the switch 45 is pressed. This causes circuit 30 to be activated and it will measure the first frequency f1 from the oscillator 20 and save it in memory. After this step is performed, which takes less than a second, the lowest LED D3 (green) comes on and stays on as a power indicator, while the switch 45 is pressed. This signals to the operator that the device can now be moved across the wall being probed. As the sensor is moved across the wall the circuit 30 is continuously measuring the second or subsequent frequency f2 from oscillator 20 and comparing it to the first frequency f1 by taking the frequency difference. When the difference exceeds a first threshold, the next LED up, LED D4 (amber) will be lit and LED D3 will go out. When the difference exceeds a second threshold, greater than the first threshold, the next LED D5 (amber) will be turned on and LED D4 will go out. When the difference exceeds a third threshold, greater than the second threshold and which indicates the presence of the leading edge of the stud, the highest LED D2 (red) goes on and the LED D5 goes out. LED D2 stays on as the thickness of the stud is traversed by the device. When the trailing edge of the device is reached, the LEDs go off and on in the reverse sequence. Thus, a user trying to find a stud, will mark the leading edge of the stud when LED D2 comes on, and will mark the trailing edge of the stud when the LED D2 goes When a user first puts the device against a wall or other surface to be probed, there is no way of telling if it is initially placed over a stud or other subsurface object or not. The device assumes that it is not. However, if by chance it is, then the subsequently found frequency difference will be negative and unless special provision is made in the programming of the microprocessor, an error will result. It is an easy matter, however, to program the microprocessor so that if the f1–f2 frequency difference is found to be negative, it means that the device was initially placed over a stud or other subsurface object. The device could be programmed to flash the LEDs or beep a buzzer in that event to alert the user to start over, placing the device in a different initial position.

Figure 3:
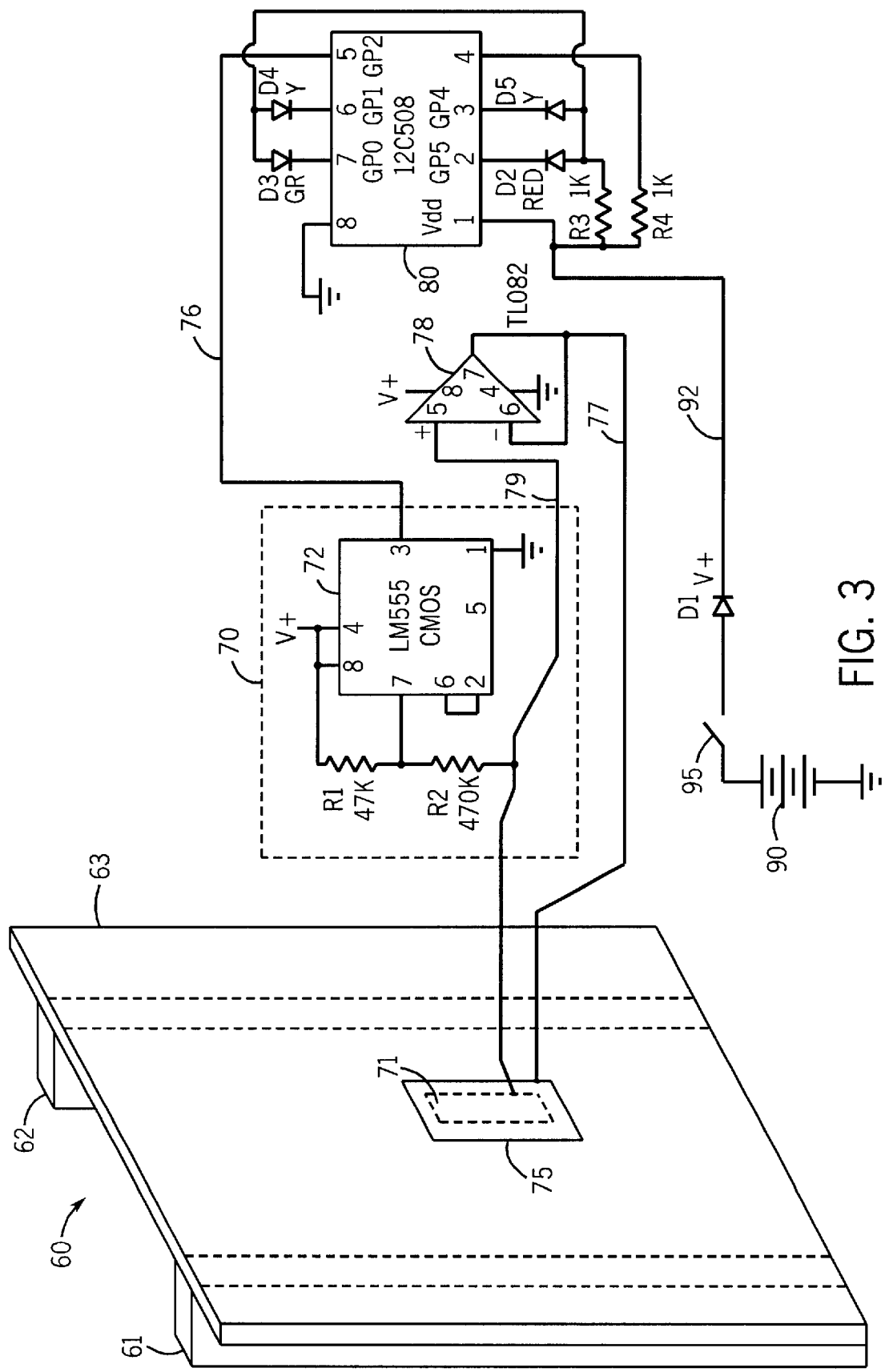
FIG. 3 is a schematic diagram of a second embodiment of a circuit for practicing the invention.

Referring to FIG. 3, there is illustrated a circuit diagram of a second embodiment of the invention. Shown on this figure is a portion of a wall structure 60, studs 61, 62 and wall board 63 to be illustrative of one way of operating the invention. In this case, it is desired to locate the positions of the hidden studs 61 and 62. As shown in FIG. 3, there is a metallic sensor plate 71 connected to a CMOS oscillator 70. The frequency of the oscillator 70 is determined by IC 72, the values of resistors R1 and R2 and the capacitance presented by the plate 71.

The capacitance of the plate 71 is determined by the surrounding medium including the wall material, the studs, the circuit and the person holding the device. It is desirable to reduce the stray capacitance as much as possible since this will improve the sensitivity of the plate 71. The capacitance of plate 71 is influenced considerably by the operator and the housing of the device.

Capacitance is related to its potential with respect to other objects. If an additional plate 75 is introduced in the vicinity of plate 71 with the same potential as plate 71, it will reduce the "stray" effects. This improves the sensitivity of the plate 71 and allows it to sense further into the wall.

The potential of plate 71 changes as the oscillator 70 operates. In a typical situation it may vary from 0 to 5 volts in amplitude. Hence the guard plate 75 must have its potential vary in the same way. This is accomplished by using a buffer amplifier 78, with a gain of one, which has the voltage of the sensor plate 71 at its input and produces a near exact replica of it at its output, which is connected to plate 75 via line 77. Hence plate 75 is driven at the same potential as plate 71.

Figure 4A:
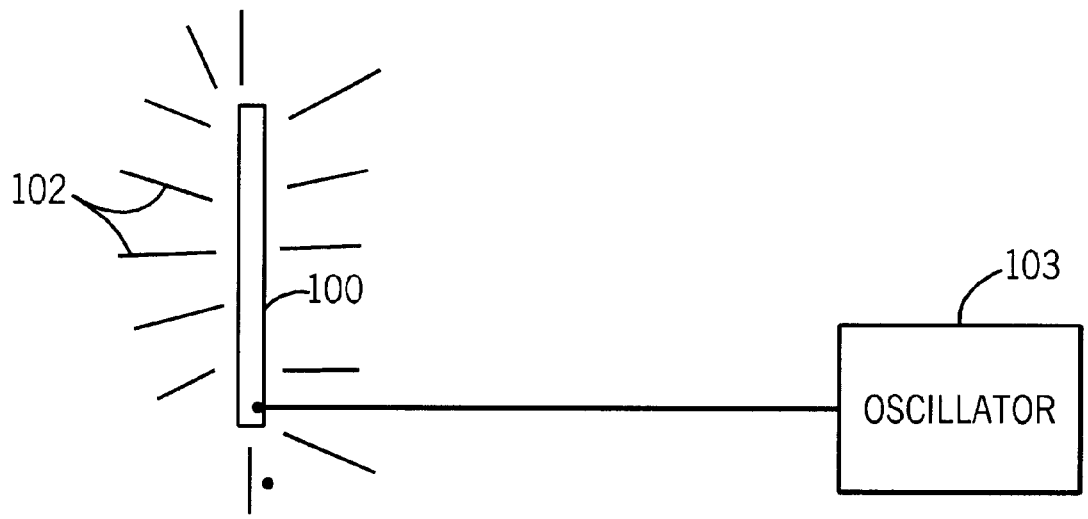
FIGS. 4A–4B are schematic diagrams illustrating a comparison of the operation of the first embodiment and the second embodiment.

Referring to FIG. 4A, a side view of a sensor plate 100 is shown to illustrate how a sensor with a single plate operates. The sensor plate 100 is connected to the oscillator 103, which causes its potential to vary. The electrical E-field lines 102 are free to go in any and all directions.

Figure 4B:
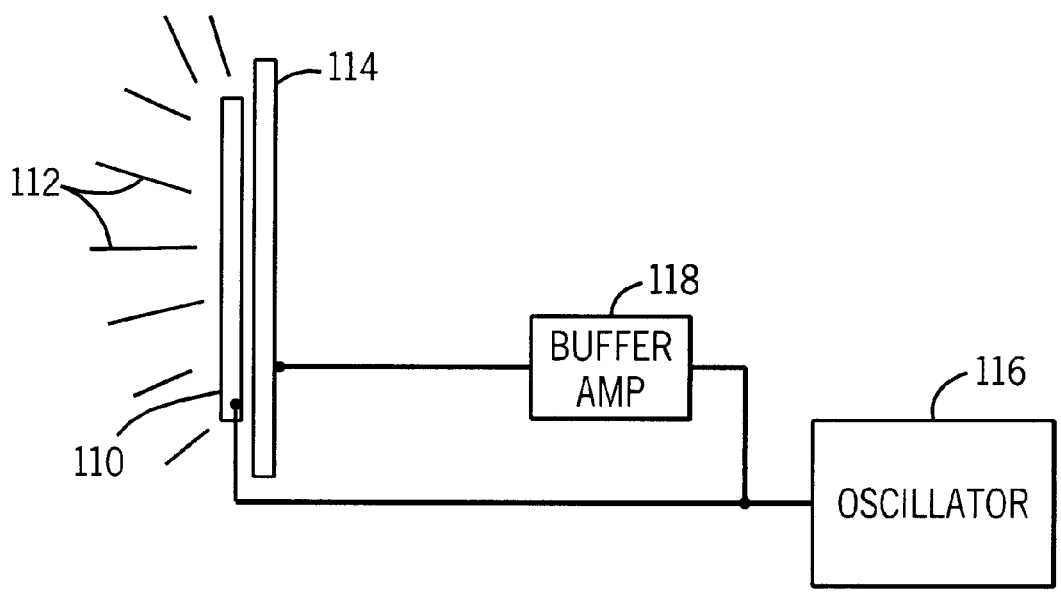
Figure 5:
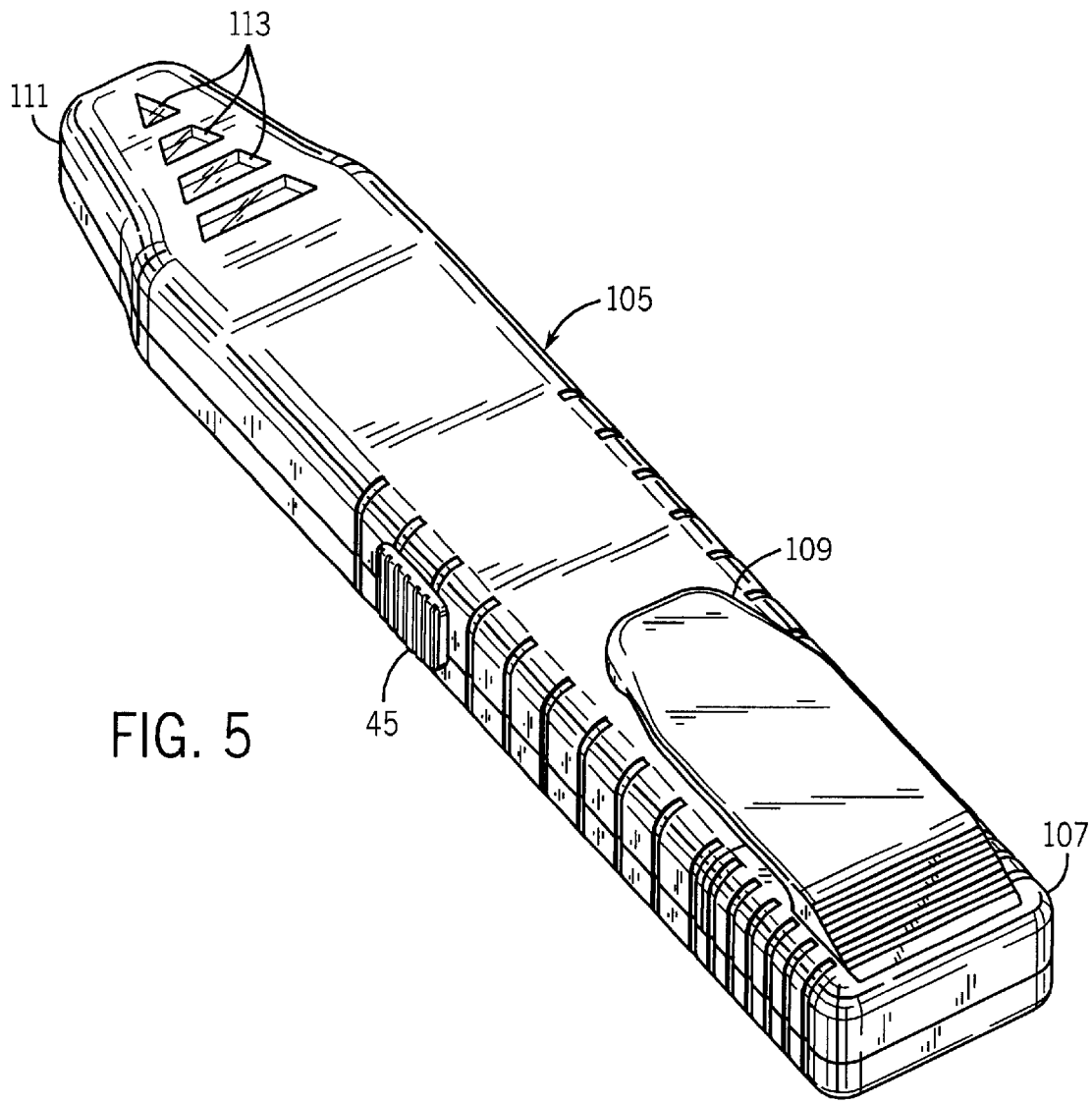
FIG. 5 is a perspective view of an electrical instrument design incorporating the invention.
Figure 10:
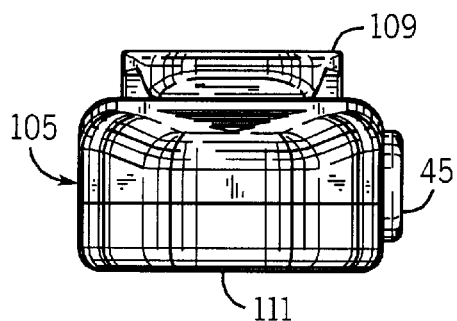
FIG. 10 is a front plan view of the instrument.
Figure 11:
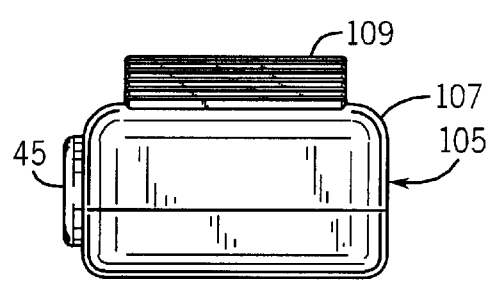
FIG. 11 is a rear plan view of the instrument.
Figure 6:
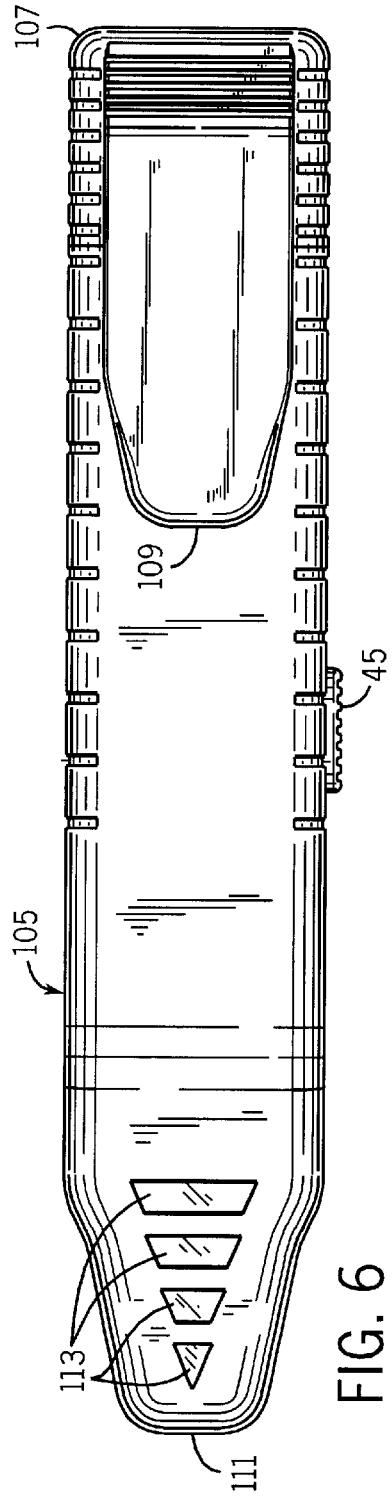
FIG. 6 is top plan view of the instrument of FIG. 5.
Figure 7:
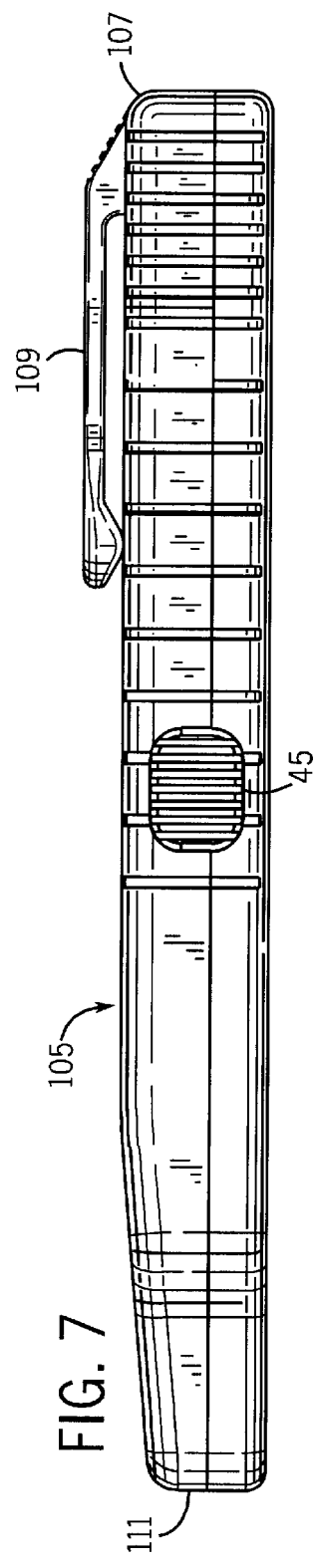
FIG. 7 is a right side plan view of the instrument.
Figure 8:
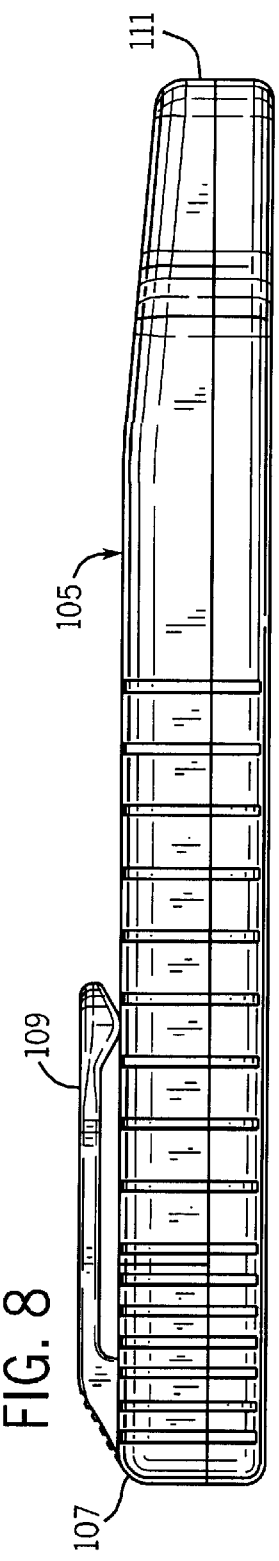
FIG. 8 is a left side plan view of the instrument.
Figure 12:
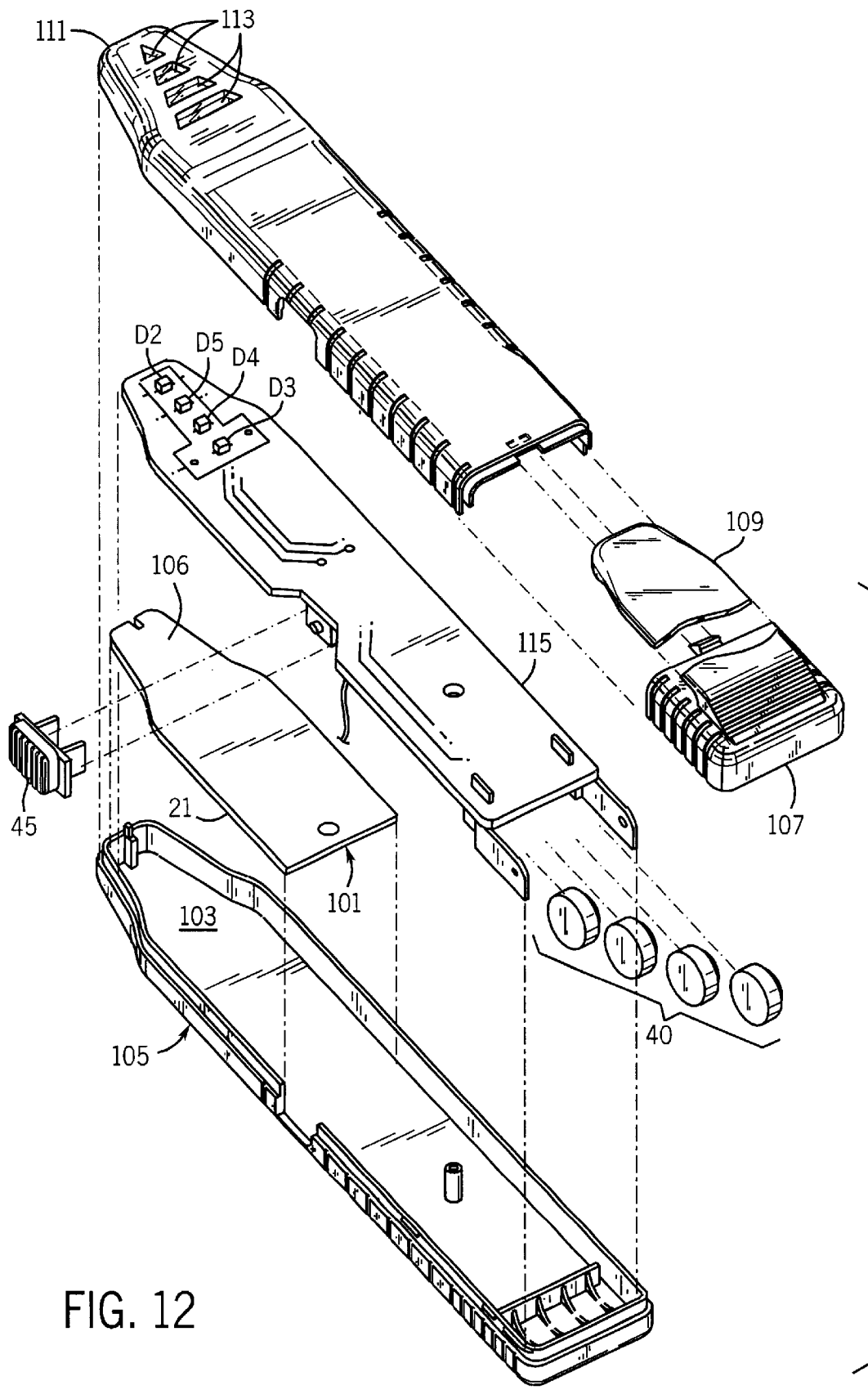
FIG. 12 is an exploded perspective view illustrating how the sensor plate, circuit board, switch and batteries are assembled in the instrument housing.
Figure 13:
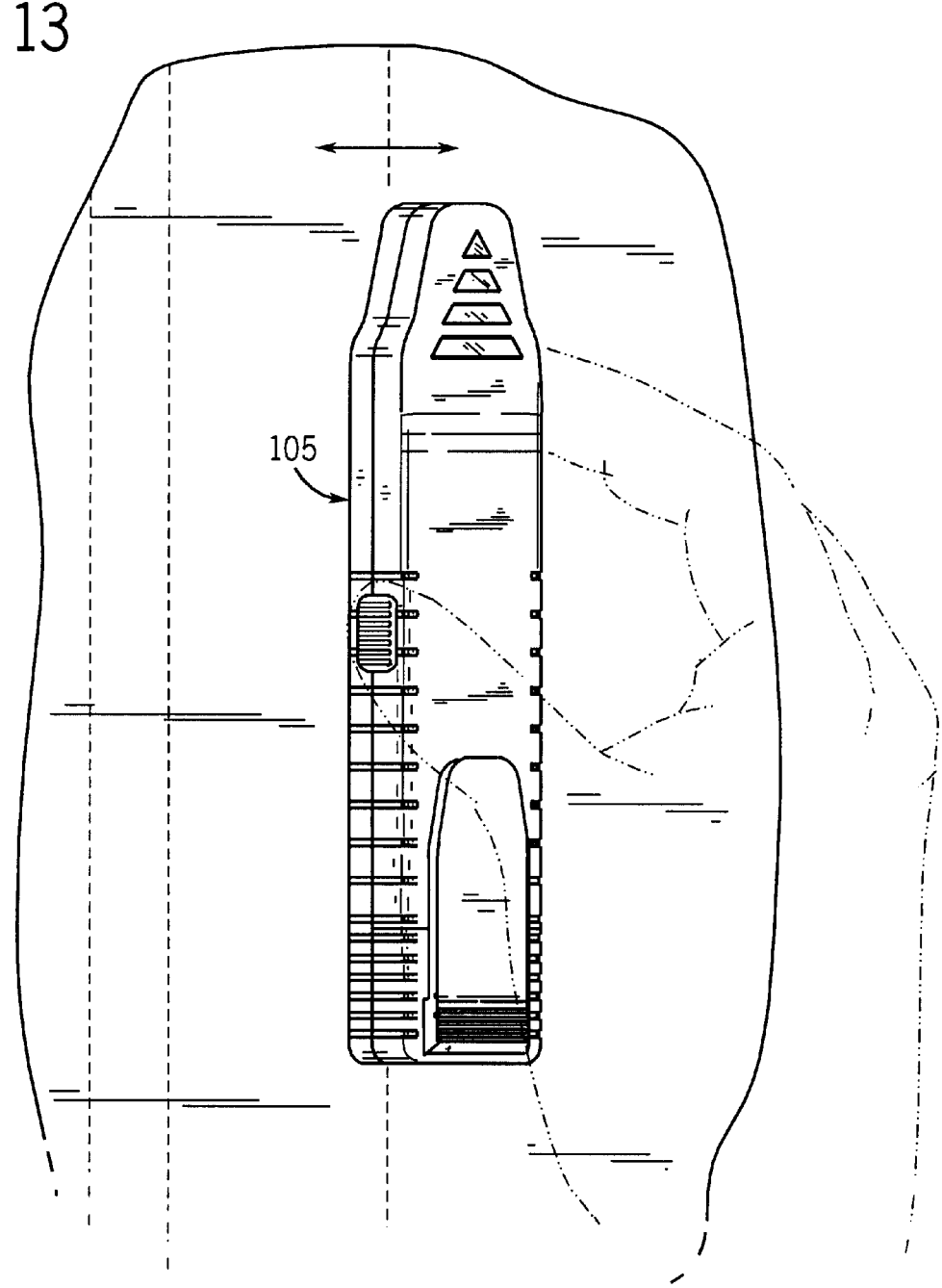
FIG. 13 is a schematic showing use of the instrument against a wall to detect a stud.

FIG. 4B illustrates how the second embodiment described above operates. In FIG. 4B, a sensor plate 10 is connected to an oscillator 116 and a guard plate 114 is driven from amplifier 118 so it has the same potential as the sensor plate. The E-field 112 is now prevented from going in the direction of the guard plate 114. This is because both plates are at the same potential and by electrical laws there can be no E-field between conductors of the same potential. With fewer E-field lines, there is less capacitance of plate 110. Hence it will be more responsive to dielectric changes in the direction opposite to the guard plate 114. The guard plate 114 may be somewhat larger than the sensor plate 10 so as to extend beyond the edges of the sensor plate 110, which redirects the E-field lines emanating from the edges of the plate 110 in the direction toward the surface being probed.

Referring back to FIG. 3, the remainder of the circuit of FIG. 3 acts in the same way as the first embodiment of FIG. 1. When the sensor plate is above a section of the wall 63 with no studs it will cause the oscillator 70 to run at frequency f1. When the sensor is above a section of the wall 63 that has a stud below it the oscillator will have a different frequency 2. The output of the oscillator 70 goes to a microprocessor circuit 80 via line 76.

The microprocessor circuit 80 is programmed to measure the frequency difference f1 minus f2. As in the first embodiment, this can be done by any suitable means. For example, the microprocessor circuit 80 will typically include a counter. The counter can be programmed to count the number of times the oscillator output signal to the microprocessor goes high in a certain period, which yields a measure of the frequency of the oscillator output. If the frequency difference between the first measured frequency and the subsequently measured frequencies exceeds an amount deemed sufficient to indicate the presence of a stud, an LED is turned on.

The circuit 80 actually has four LEDs D2, D3, D4 and D5 that can be activated at different amounts of frequency change. This is illustrated in more detail in FIG. 2. More or fewer LEDs could be used as indicators depending upon resolution and cost considerations.

The circuit is powered by batteries 90 through protective diode D1 and line 92. Resistor R3 is used to limit the current in the LEDs. Resistor R4 is used for a power on reset for circuit 80. Switch 95 is pressed to enable power to circuit from the battery 90 to circuit 80.

The microprocessor is capable of detecting very small changes in the frequency of the oscillator, which improves the sensitivity of the device and permits making the device relatively small. FIGS. 5–13 illustrate the design of an electrical instrument, which may include either of the two previously described circuits. As illustrated, this instrument is generally pen-light sized, able to easily fit into a breast pocket. In the preferred embodiment, the device is approximately 1 inch wide, 19/32 inches thick (not including the pocket clip) and 5 9/16 inches long. The housing 105 is provided with a pocket clip 109, integrally molded as part of the battery cover 107, to help hold the device in a user's breast pocket, since the device is small enough to fit, being at least three times longer than it is wide, and in the case of the embodiment disclosed, being over five times longer than it is wide. To be of material benefit over prior art devices, it is preferred that the locator be less than two inches wide, which is more than accommodated by the preferred embodiment, since it is only 1 inch wide.

The instrument in FIGS. 5–13 has been labeled with reference numbers as if it includes the first circuit, of FIG. 1. If so, the metal sensor plate 21 can be provided on the bottom side of a printed circuit board 101, and fixed in the housing, for example by an adhesive, so the exposed surface of the plate is against bottom wall 103 of housing 105 so as to minimize any air gap between the plate 21 and the surface being probed. The plate 21 may be provided as the copper layer commonly provided as part of an ordinary printed circuit board. If tile device is made to include the second circuit of FIG. 3, the circuit board 100 can be provided with metal (typically copper) layers on both sides, with the layer on side 106 being the guard plate 75, and the layer 71 being on the lower side, as is layer 21. The lower side sensor plate may be etched so as to make it smaller than the upper side guard plate. The other circuits, i.e., the oscillator, microprocessor, LED and buffer amp (if applicable) circuits, are provided on circuit board 115, which is secured in the housing 105 as far away as possible from the sensor plate 21.

The top end of the housing 105 tapers in width to a blunt point 111, to give an operator a better approximation of the center of the device. Transparent or translucent windows 113 centered laterally on the front surface of the housing 105 are aligned with the respective LEDs D2–D5 and also taper in width toward the top to a sharper point, also to help the operator locate the center of the housing, and therefore the edge of a stud or other subsurface object.

Variations and modifications to the preferred embodiments described will be obvious to persons skilled in the art without deviating from the spirit of the invention. Therefore, the invention should not be limited to the preferred embodiments described, but should be defined by the claims which follow.

We claim:

1. A hand held subsurface object locator, comprising:
   a housing;
   circuitry and a power source contained in the housing, wherein said circuitry comprises a timer, a microprocessor circuit and a capacitor plate, said capacitor plate being within the housing adjacent and parallel to a rear wall of the housing, said circuitry being responsive to changes in capacitance of the capacitor plate caused by sliding said housing over a wall surface, with the rear wall of the housing adjacent to the wall surface, said changes in capacitance being caused by the presence of a substratum object which is behind the wall surface, to detect substratum objects hidden behind a surface which is probed with the locator by sliding the locator along the surface,
   wherein said housing and capacitor plate are each less than two inches wide;
   wherein said housing is at least three times as long as it is wide and the capacitor plate is shorter than the housing; and
   wherein said housing has a pocket clip on a front side wall of the housing at one end and at least one indicator on the front side wall of the housing at the other end.

2. The improvement of claim 1, wherein said pocket clip is affixed to a battery compartment door at said one end of said housing, and the other end of said housing is tapered.

3. The improvement of claim 2, wherein said other end of said housing includes one or more indicators which taper toward said other end.

4. A subsurface object locator as claimed in claim 1, wherein said housing includes a plurality of signal indicators, and wherein said indicators are activated serially without overlapping activation at an approximate leading edge of said subsurface object and are serially deactivated without overlapping activation at an approximate trailing edge of said object.

5. A subsurface object locator as claimed in claim 4, wherein said indicators taper toward an end of said detector, said indicator closest to an end of said locator indicating the presence of an object.

* * * * *

UNITED STATES PATENT AND TRADEMARK OFFICE
CERTIFICATE OF CORRECTION

PATENT NO. : 6,593,754 B1  Page 1 of 1
DATED : July 15, 2003
INVENTOR(S) : George R. Steber et al.

It is certified that error appears in the above-identified patent and that said Letters Patent is hereby corrected as shown below:

Column 1,
Line 24, "arc" should be -- are --.
Line 42, "modem" should be -- modern --.

Column 3,
Line 44, "IN270" should be -- 1N270 --.

Column 4,
Line 27, "goes When" should be -- goes off. When --.

Column 5,
Lines 11 and 21, "10" should be -- 110 --.
Line 31, "2" should be -- f2 --.

Column 6,
Line 17, "tile" should be -- the --.

Signed and Sealed this

Twentieth Day of January, 2004

JON W. DUDAS
*Acting Director of the United States Patent and Trademark Office*